United States Patent
von Allmen

(10) Patent No.: US 11,908,087 B2
(45) Date of Patent: Feb. 20, 2024

(54) ANALYTICAL LABORATORY

(71) Applicant: Roche Diagnostics Operations, Inc., Indianapolis, IN (US)

(72) Inventor: Bernhard von Allmen, Seengen (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 496 days.

(21) Appl. No.: 16/831,950

(22) Filed: Mar. 27, 2020

(65) Prior Publication Data
US 2020/0312448 A1    Oct. 1, 2020

(30) Foreign Application Priority Data
Mar. 29, 2019  (EP) ..................................... 19166340

(51) Int. Cl.
| | | |
|---|---|---|
| *G06T 19/00* | (2011.01) | |
| *G16H 40/40* | (2018.01) | |
| *G02B 27/01* | (2006.01) | |
| *G06F 3/01* | (2006.01) | |
| *H04N 5/33* | (2023.01) | |
| *H04N 7/18* | (2006.01) | |

(52) U.S. Cl.
CPC ........ *G06T 19/006* (2013.01); *G02B 27/0172* (2013.01); *G06F 3/011* (2013.01); *G16H 40/40* (2018.01); *H04N 5/33* (2013.01); *H04N 7/185* (2013.01); *G02B 2027/0178* (2013.01)

(58) Field of Classification Search
None
See application file for complete search history.

(56) References Cited

U.S. PATENT DOCUMENTS

| | | | |
|---|---|---|---|
| 6,049,775 A * | 4/2000 | Gertner | ............ G06Q 10/06395 |
| | | | 715/752 |
| 8,394,636 B2 | 3/2013 | Nishikiori et al. | |
| 9,179,105 B1 | 11/2015 | Zeira et al. | |

(Continued)

FOREIGN PATENT DOCUMENTS

| | | |
|---|---|---|
| CN | 109032088 A | 12/2018 |
| EP | 1821483 A1 | 8/2007 |

(Continued)

OTHER PUBLICATIONS

European Search Report dated Sep. 5, 2019, in Application No. EP 19166340.0, 2 pp.

(Continued)

*Primary Examiner* — Jwalant Amin
(74) *Attorney, Agent, or Firm* — Roche Diagnostics Operations, Inc.

(57) ABSTRACT

A productivity tool for an analytical laboratory is presented. The productivity tool provides aggregated operational status of all laboratory instruments within an analytical laboratory, even without access to their respective internal data stream (i.e., legacy and third party instruments) by determining operational status of a first group of instruments by capturing and processing internal data streams comprising data indicative of an operational status. The productivity tool also determines operational status of a second group of instruments by capturing and processing external surveillance stream(s) of one or more laboratory instrument(s) of the second group.

20 Claims, 6 Drawing Sheets

(56) References Cited

U.S. PATENT DOCUMENTS

| | | | | |
|---|---|---|---|---|
| 2007/0168970 A1* | 7/2007 | Li | ............... | G06F 11/3696 |
| | | | | 717/124 |
| 2009/0222746 A1* | 9/2009 | Chirica | ............ | G06Q 10/06 |
| | | | | 715/802 |
| 2010/0082279 A1* | 4/2010 | DeSimas | .......... | G01N 31/00 |
| | | | | 702/182 |
| 2010/0271479 A1 | 10/2010 | Heydlauf | | |
| 2011/0153096 A1* | 6/2011 | Pal | ................ | F03D 7/047 |
| | | | | 290/44 |
| 2012/0219157 A1* | 8/2012 | Hosaka | ........... | G01H 3/08 |
| | | | | 381/56 |
| 2014/0247347 A1* | 9/2014 | McNeill | .......... | H04N 7/18 |
| | | | | 382/103 |
| 2014/0359752 A1 | 12/2014 | Swaminathan | | |
| 2017/0227953 A1* | 8/2017 | Nagase | ........... | G05B 23/0208 |
| 2020/0141607 A1* | 5/2020 | Ikeda | ............. | H04M 11/00 |

FOREIGN PATENT DOCUMENTS

| | | |
|---|---|---|
| JP | H10-227797 A | 8/1998 |
| JP | 2005-106746 A | 4/2005 |
| JP | 2015-172509 A | 10/2015 |
| WO | 2011/117817 A2 | 9/2011 |
| WO | 2018/213400 A1 | 11/2018 |

OTHER PUBLICATIONS

Office Action dated Aug. 30, 2023, in Application No. JP 2020-055380, 5 pp.

* cited by examiner

ANALYTICAL LABORATORY

CROSS-REFERENCE TO RELATED APPLICATIONS

This application is a continuation of EP 19166340.0, filed Mar. 29, 2019, which is hereby incorporated by reference.

BACKGROUND

The present disclosure generally relates to an analytical laboratory, in particular, an in-vitro diagnostic laboratory, a computer implemented method of operating an analytical laboratory, as well as a computer program product comprising instruction for operating an analytical laboratory.

In vitro diagnostic testing can have a major effect on clinical decisions, providing physicians with pivotal information. In analytical laboratories, in particular, in-vitro diagnostic laboratories, a multitude of analyses on biological samples are executed by laboratory instruments in order to determine physiological and biochemical states of patients, which can be indicative of a disease, nutrition habits, drug effectiveness, organ function and the like.

Conventionally, laboratory users/technicians have to physically observe all laboratory instruments to ensure proper operation. With rising complexity and scale of analytical laboratories, there is a need to provide productivity tools to manage the multitude of laboratory instruments within large analytical laboratories. One particular requirement of such productivity tools is to provide up-to-date and aggregated information on the operational status of the laboratory instruments to enable laboratory users/technicians to monitor the laboratory instruments with reduced effort and less risk of oversight.

Several productivity solutions are known which provide a dashboard type consolidated monitor of laboratory instruments. Such productivity solutions are of great use for the laboratory users/technicians only if they allow monitoring of most—or even all—laboratory instruments within large analytical laboratories. Otherwise, the laboratory users/technicians would still need to individually monitor a subset of instruments, a sub-optimal solution. However, known solutions require a data connection to the laboratory instruments monitored, in particular, access to the internal data stream(s) to and from the laboratory instruments. In practice, a data connection to all laboratory instruments is difficult to establish for several reasons: In most large analytical laboratories, the various laboratory instruments are from different vendors/providers. One particular provider of a productivity tool to monitor a laboratory is often not allowed access to the data connection of laboratory instruments of other vendors, for technological or security reasons or because certain instruments are designed as closed systems. Technological reasons—for not having access to the internal data stream to/from an instrument—comprise legacy instruments, which have not been designed with connectivity in mind, incompatible communication technologies, and the like. On the other hand, certain vendors intentionally design their instruments as closed systems to prevent competitors' access to instrument data. In addition, privacy regulations/concerns also pose limitations to access to the internal data stream of laboratory instruments.

Hence, there is a need for a productivity tool for a laboratory system that provides aggregated operational status of all laboratory instruments within an analytical laboratory, even without access to their respective internal data stream such as for legacy and/or third party instruments.

SUMMARY

According to the present disclosure, a system and method for determining operational status of a plurality of laboratory instrument are disclosed. The method can comprise communicatively connecting a control unit to one or more laboratory instrument(s) of a first group, capturing one or more external surveillance stream(s) of one or more of a second group of laboratory instrument(s) by a surveillance device, and receiving an internal data stream from one or more laboratory instrument(s) of the first group by the control unit. The internal data stream(s) can comprise data indicative of an operational status of one or more laboratory instrument(s) of the first group. The method can also comprise receiving the external surveillance stream(s) of the laboratory instrument(s) of the second group by the control unit, processing the internal data stream(s) from the laboratory instrument(s) of the first group by the control unit to extract an operational status of one or more laboratory instrument(s) of the first group, processing the external surveillance stream(s) of the laboratory instrument(s) of the second group by the control unit to detect an operational status of one or more laboratory instrument(s) of the second group, outputting the operational status of any one of the laboratory instrument(s) of the first group via a lab monitoring interface, and outputting the operational status of any one of the laboratory instrument(s) of the second group via a lab monitoring interface.

Accordingly, it is a feature of the embodiments of the present disclosure to provide a productivity tool for a laboratory system that provides aggregated operational status of all laboratory instruments within an analytical laboratory, even without access to their respective internal data stream such as for legacy and/or third party instruments. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
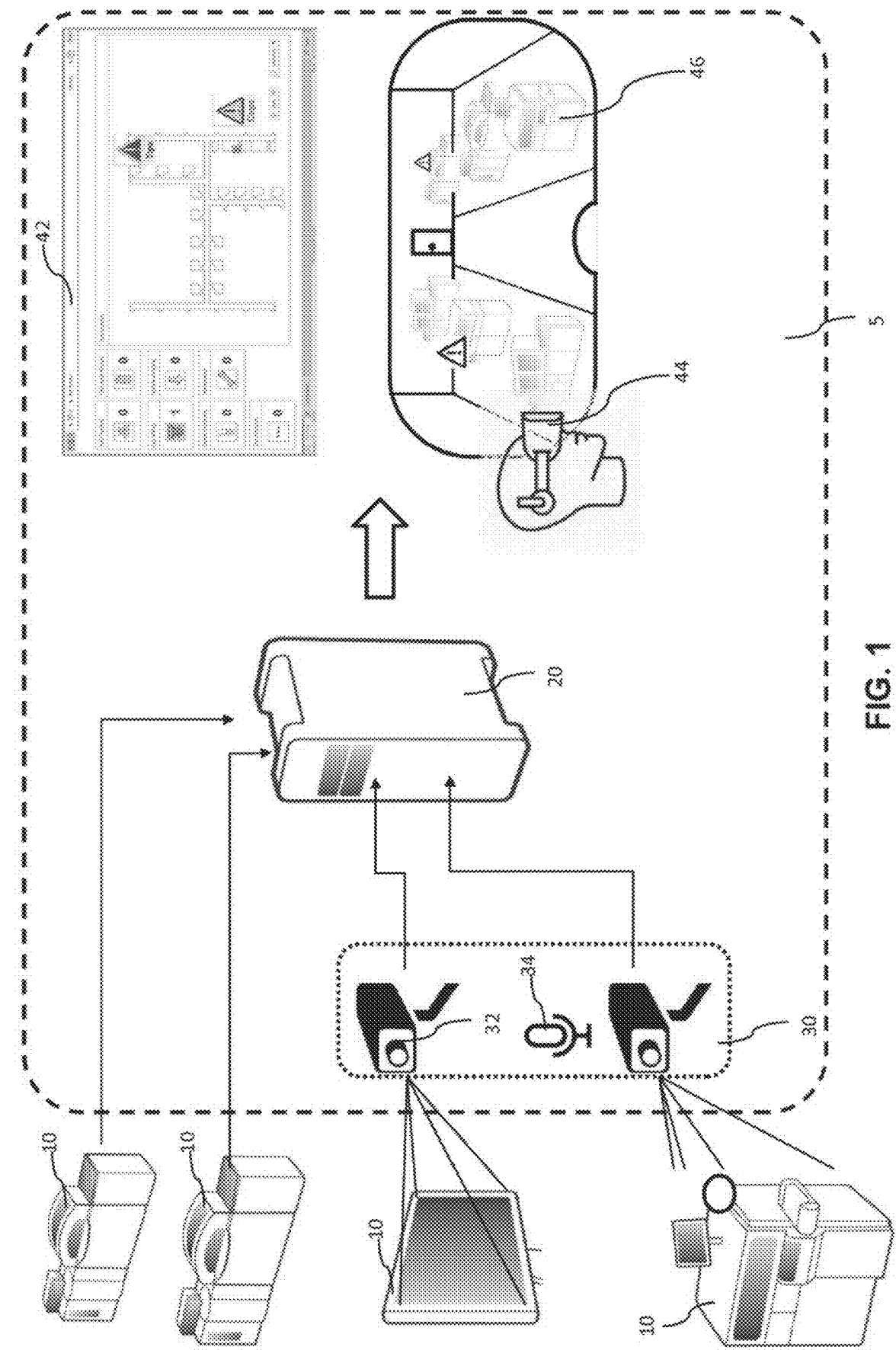
FIG. 1 illustrates a highly schematic block diagram of an analytical laboratory comprising a herein disclosed productivity tool according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The embodiments herein disclosed address the need for a productivity tool for a laboratory system that provides aggregated operational status of all laboratory instruments within an analytical laboratory, even without access to their respective internal data stream such as for legacy and/or third party instruments by combining determining operational status of a first group of instruments by capturing and processing internal data streams comprising data indicative of an operational status, determining operational status of a second group of instruments by capturing and processing external surveillance stream(s) of one or more laboratory instrument(s) of the second group, and outputting the operational status of any one of the laboratory instrument(s) of the first and/or second group via the lab monitoring interface.

The operational status of a laboratory instrument can comprise indications related to the instrument's readiness to process biological samples, including but not limited to
- Indications whether the analytical instrument is switched on/off or in a low power mode (sleep, hibernate);
- Indications whether modules of the analytical instrument required to process biological samples are operational or not;
- Indications whether consumables required to process biological samples are available; and
- Indications whether quality control and/or calibration steps required before process biological samples are available are up-to-date and valid.

According to some embodiments, the productivity tool for an analytical laboratory can comprise a control unit, a surveillance device and a lab monitoring interface. The control unit can be communicatively connectable to one or more laboratory instrument(s) of a first group in order to capture an internal data stream from the laboratory instrument(s) of the first group.

According to some embodiments, the internal data stream (s) can comprise signals from a user interface of the instrument, signals of human interaction devices of the instrument (such as a keyboard, a mouse and/or a touchscreen), log files of the laboratory instrument(s), external data communication to and from a laboratory middleware or laboratory information system (LIS), and/or alert signals of the laboratory instrument. The internal data stream(s) can, for example, comprise any kind of signal and data, which directly indicates an operational status of an instrument.

Surveillance device(s) external to the laboratory instrument(s) can be arranged to capture one or more external surveillance stream(s) of one or more of a second group of laboratory instrument(s). The second group of laboratory instrument(s) can, for example, comprise instruments for which a communicative connection to capture an internal data stream indicative of their operational status is impeded or not possible (closed systems, different vendors or legacy instruments).

According to some embodiments, the laboratory instrument(s) of the first group can provide a type of data connection for internal data stream(s) that can be different from a type of data connection for internal data stream(s) of the laboratory instrument(s) of the second group. 'Type of data connection' here can refer to external accessibility to the internal data stream(s), e.g. type of interface, type of data format, type of encryption, and/or type of access control. In one example, a type of data connection for internal data stream(s) of the of the laboratory instrument(s) of the first group can differ from a type of data connection for internal data stream(s) of the of the laboratory instrument(s) of the second group in that the laboratory instrument(s) of the first group may provide a data connection for accessing internal data stream(s) and the laboratory instrument(s) of the second group may not provide a data connection for accessing internal data stream(s), as it, for example, can be the case for legacy devices. In another example, the first group can comprise of laboratory instrument(s) of a first vendor and the second group can comprises of laboratory instrument(s) of other vendors, wherein each vendor can control the access to internal data stream(s) using a different access control so that the first vendor cannot readily access the internal data stream(s) of the other vendors.

In order to collect operational status of both groups of laboratory instruments, the control unit can be configured to receive and process both the internal data stream(s) from the laboratory instrument(s) of the first group and the external surveillance stream(s) of the laboratory instrument(s) of the second group. In processing the internal data stream(s) from the laboratory instrument(s), the control unit can be configured to extract the operational status of one or more laboratory instrument(s) of the first group, wherein the internal data stream(s) can, for example, readily comprise data indicative of the operational status. In processing the external surveillance stream(s) of the laboratory instrument(s) of the second group, the control unit can be configured to detect an operational status of one or more laboratory instrument(s) of the second group, wherein the processing can, for example, comprise processing of the external surveillance stream(s) to identify elements of the internal data stream(s) which can be representative of a particular operational status.

As it is determined, the operational status of any one of the laboratory instrument(s) of the first and/or second group can be output via the lab monitoring interface.

These embodiments can be advantageous as they can allow overall (all-inclusive) monitoring of an entire laboratory comprising instrument(s) both with access to their internal data stream (e.g. fully integrated or open systems) and without access to their internal data stream (e.g. legacy systems or closed systems).

Certain terms will be used in this patent application, the formulation of which should not be interpreted to be limited by the specific term chosen, but as to relate to the general concept behind the specific term.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The term 'analyte' can be a component of a sample to be analyzed, e.g. molecules of various sizes, ions, proteins, metabolites and the like. Information gathered on an analyte may be used to evaluate the impact of the administration of drugs on the organism or on particular tissues or to make a diagnosis. Thus, 'analyte' can be a general term for substances for which information about presence, absence and/or concentration is intended. Examples of analytes are e.g., glucose, coagulation parameters, endogenic proteins (e.g., proteins released from the heart muscle), metabolites, nucleic acids and so on.

The term 'analysis or 'analytical test' as used herein can encompass a laboratory procedure characterizing a parameter of a biological sample for qualitatively assessing or quantitatively measuring the presence or amount or the functional activity of an analyte.

The term 'reagent' as used herein can refer to materials for performing an analysis of analytes, including reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents.

The term 'laboratory instrument' as used herein can encompass any apparatus or apparatus component operable to execute one or more processing steps/workflow steps on one or more biological samples and/or one or more reagents. The expression 'processing steps' thereby can refer to physically executed processing steps such as centrifugation, aliquotation, sample analysis and the like. The term 'instrument' can cover pre-analytical instruments, post-analytical instruments, and, also, analytical instruments.

The term 'analyzer'/'analytical instrument' as used herein can encompass any apparatus or apparatus component configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzer can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'pre-analytical instrument' as used herein can encompass any apparatus or apparatus component that is configured to perform one or more pre-analytical processing steps/workflow steps comprising—but not limited to—centrifugation, resuspension (e.g., by mixing or vortexing), capping, decapping, recapping, sorting, tube type identification, sample quality determination and/or aliquotation steps. The processing steps may also comprise adding chemicals or buffers to a sample, concentrating a sample, incubating a sample, and the like.

The term 'post-analytical instrument' as used herein can encompass any apparatus or apparatus component that is configured to perform one or more post-analytical processing steps/workflow steps comprising—but not limited to—sample unloading, transport, recapping, decapping, temporary storage/buffering, archiving (refrigerated or not), retrieval and/or disposal.

The term 'sample transportation system' as used herein can encompass any apparatus or apparatus component that is configured to transport sample carriers (each holding one or more sample containers) between laboratory instruments. In particular, the sample transportation system can be a one dimensional conveyor-belt based system, a two-dimensional transportation system (such as a magnetic sample carrier transport system) or a combination thereof.

The term 'control unit' as used herein can encompass any physical or virtual processing device configurable to control a laboratory instrument/system comprising one or more laboratory instruments in a way that workflow(s) and workflow step(s) can be conducted by the laboratory instrument/system. The control unit may, for example, instruct the laboratory instrument/system to conduct pre-analytical, post analytical and analytical workflow(s)/workflow step(s). The control unit may receive information from a data management unit regarding which steps need to be performed with a certain sample. In some embodiments, the control unit may be integral with a data management unit, may be comprised by a server computer and/or be part of one laboratory instrument or even distributed across multiple instruments of the analytical laboratory. The control unit may, for instance, be embodied as a programmable logic controller running a computer-readable program provided with instructions to perform operations.

A 'storage unit' or 'database' can be a unit for digitally storing and managing data such as a memory, hard disk or cloud storage. This may involve data relating to biological sample(s) to be processed by the automated system. The data management unit may be connected to an LIS (laboratory information system) and/or an HIS (hospital information system). The data management unit can be a unit within or co-located with a laboratory instrument. It may be part of the control unit. Alternatively, the database may be a unit remotely located. For instance, it may be embodied in a computer connected via a communication network.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

An 'analytical laboratory' as used herein can comprise a control unit operatively coupled to one or more instruments, e.g., one or more analytical, pre-analytical, and/or post-analytical instruments, wherein the control unit can be operable to control the instruments. In addition, the control unit may be operable to evaluate and/or process gathered analysis data, to control the loading, storing and/or unloading of samples to and/or from any one of the analyzers, to initialize an analysis or hardware or software operations of the analysis system used for preparing the samples, sample tubes or reagents for said analysis and the like. The instruments of an analytical laboratory and the control unit can be interconnected by a communication network.

Particular embodiments will now be described with reference to the figures. FIG. 1 shows a highly schematic block diagram of an analytical laboratory comprising a productivity tool 5. The analytical laboratory 1 can comprise a plurality of laboratory instrument 10 configured to perform one or more processing step(s) on a biological sample such as, for example, to determine the presence, absence and/or concentration of an analyte. The laboratory instruments 10 can e.g., be divided into two groups by their level of connectivity for the purpose of operational status monitoring. Laboratory instrument(s) 10 of the first group 10.1 can e.g., comprise instruments 10 that can allow the capturing of their internal data stream(s) to an extent to enable extraction of data indicative of their operational status (e.g., fully integrated instruments). Laboratory instruments 10 of the second group 10.2 can e.g., comprise instruments 10 that may not allow access to their internal data stream(s) to an extent to enable extraction of data indicative of their operational status (e.g., closed systems or legacy instruments). According to some embodiments, the first group can be comprised in the second group and, according to some specific embodiments; the second group may not be (fully) comprised in the first group. According to some other embodiments, the two groups can be disjointed from one another.

As also shown on FIG. 1, the productivity tool 5 (shown as a whole with a dashed-line rounded rectangle) can comprise a control unit 20 communicatively connectable to one or more laboratory instrument(s) 10 of a first group 10.1. The control unit 20 can be configured to receive the internal data stream(s) from the laboratory instrument(s) 10 of the first group 10.1 and to process the internal data stream(s) from the laboratory instrument(s) 10 of the first group 10.1 to extract the operational status of one or more laboratory instrument(s) 10 of the first group 10.1. The internal data stream(s) of the one or more laboratory instrument(s) 10 of a first group 10.1 can comprise (but is not limited to) data exchanged between modules of the instruments such as, for example data related to a status of such modules; data to and from peripherals (such as human interaction devices of the instruments, e.g., keyboard, mouse, touch panel); data exchanged by the instrument with a laboratory information system or middleware such as, for example, data representative of the operational status of the instrument; data to a display module of the instrument such as the video signal to a screen; and/or log files of the instrument.

In order to enable monitoring of laboratory instrument(s) 10 of the second group 10.2, the productivity tool 5 can further comprise a surveillance device 30 (shown as a whole with a dotted-line rounded rectangle) external to the laboratory instrument(s) 10 arranged to capture one or more external surveillance stream(s) of one or more of a second group 10.2 of laboratory instrument(s) 10. Correspondingly, the control unit 20 can be configured to process the external surveillance stream(s) of the laboratory instrument(s) 10 of the second group 10.2 to detect an operational status of one or more laboratory instrument(s) 10 of the second group 10.2. In one embodiment, the control unit 20 can be configured to compare characteristics of the surveillance stream with a collection of known characteristics (stored for example in a database), each of the known characteristics being indicative of a particular operational status of a laboratory instrument.

According to some embodiments, as illustrated on FIG. 1, the surveillance device 30 can comprise a video camera 32. According to some embodiments, the video camera 32 can be designed for taking thermal images. The video camera 32 can be external to the laboratory instrument 10 and can be arranged to capture a video signal of one or more of the second group 10.2 of laboratory instrument(s) 10 as part of the external surveillance stream(s). Correspondingly, the control unit 20 can be configured to detect an operational status by analyzing the video signal of the one or more of a second group 10.2 of laboratory instrument(s) 10. The control unit 20 can e.g., be configured to detect changes of a user interface of the laboratory instrument(s) 10, e.g., changes of color and/or the appearance of one or more icons of bright color; and/or detect movement and/or position of at least a part of the laboratory instrument(s) 10, e.g., an open or closed position of compartments for loading consumables of the laboratory instrument(s) 10; and/or detect visual status indicators, e.g., status LEDs arranged on a housing of the laboratory instrument(s) 10.

In order for the control unit 20 to be able to determine the operational status of the instruments 10 based on the video signal from the video camera 32, the control unit 20, according to some embodiments, can use image recognition to identify one or more of a collection of symbols/icons from a database within the video signal, each of the symbols/icons being associated with one or more operational status.

Similarly, according to embodiments, the control unit 20 can use image recognition to identify deviations in the video signal from one or more of a collection (stored in a database) of known movements/positions of parts of the surveilled laboratory instrument 10, a deviation being indicative of a potential malfunction.

According to further embodiments, the video camera 32 can be configured to capture a thermal image of one or more of the second group 10.2 of laboratory instrument(s) 10. The control unit 20 can be configured to determine an operational temperature of at least a part of the laboratory instrument(s) 10 to determine the operational status of a laboratory instrument 10 such as, for example, to distinguish between a normal and abnormal operational status of the respective laboratory instrument(s) 10, indicated by an overheating of the laboratory instrument 10 or parts thereof.

The surveillance device 30 can comprise a microphone 34, e.g., in addition to the video camera 32 as illustrated in FIG. 1. The microphone 34 can be arranged to capture operational noise of one or more of the second group 10.2 of laboratory instrument(s) 10. The control unit 20 can be configured to determine the operational status of a laboratory instrument 10 by analyzing its operational noise, e.g., by distinguishing between a normal and abnormal operational status of the respective laboratory instrument(s) 10. According to some embodiments, the control unit 20 can use pattern recognition to identify deviations in the signals from the microphone 34 from a collection (e.g., stored in a database) of known operational noises/frequencies of parts of the surveilled laboratory instrument 10, a deviation being indicative of a potential malfunction.

After the internal data stream(s) and/or the external surveillance stream(s) have been processed, the productivity tool 5, e.g., its control unit 20, can be configured to output the operational status of any one of the laboratory instrument(s) 10 of the first and/or second group via the lab monitoring interface 40. The output can e.g., be made by outputting indications such as displaying graphical and/or textual representation on a display. The productivity tool 5 can be designed so that an operator can interact with the lab monitoring interface 40 to adjust the indication of the operational status and optionally, also the level of detail thereof.

FIG. 1 shows highly schematic illustrations of two possible embodiments of the proposed lab monitoring interface 40, namely an operational status dashboard 42 and an augmented reality device 44. These will be described in more detail with relation to FIGS. 3/4 and 5 respectively.

Figure 2:
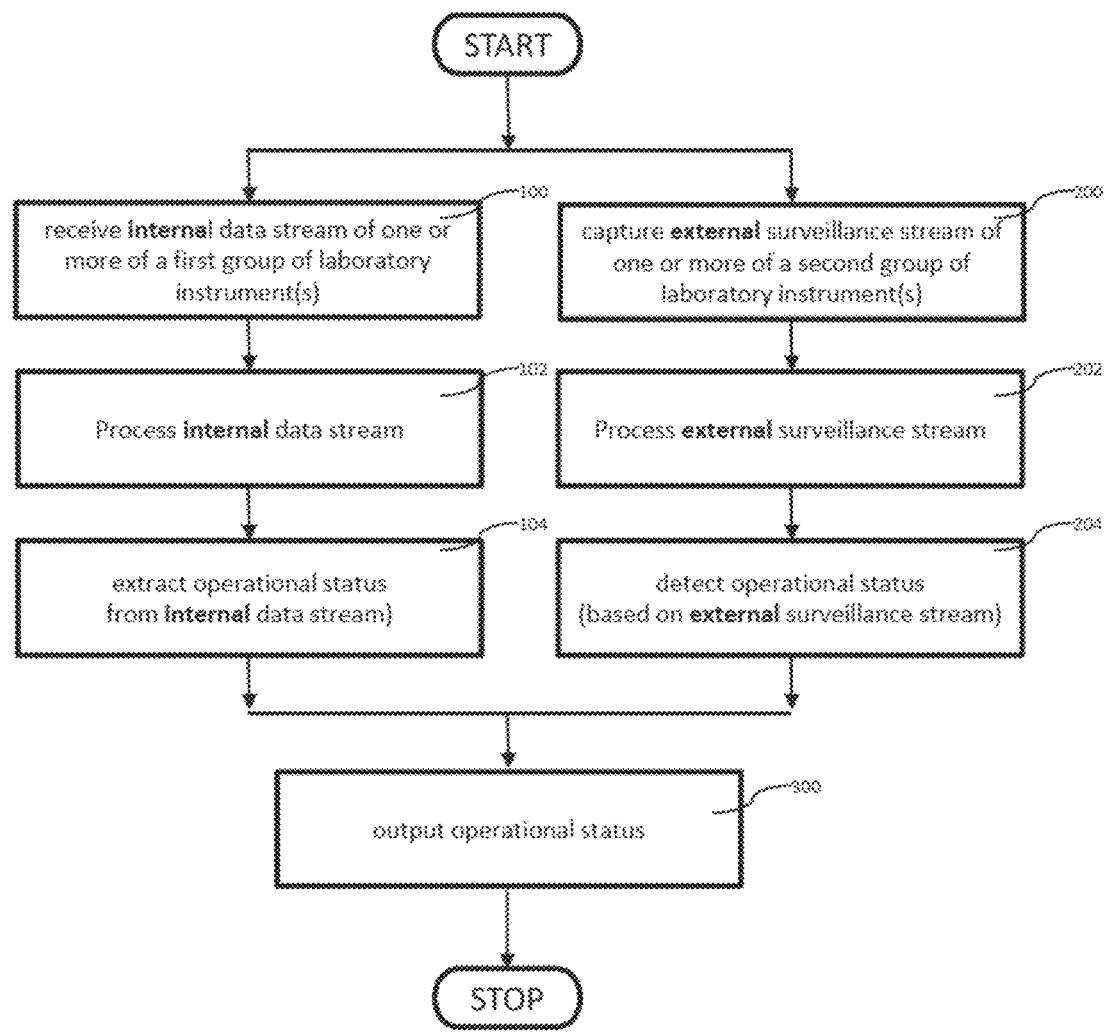
FIG. 2 illustrates a flowchart illustrating a method for determining operational status of a plurality of laboratory instrument(s) according to an embodiment of the present disclosure.

Turning now to FIG. 2, embodiments of the disclosed computer implemented method for determining operational status of a plurality of laboratory instrument(s) will be described.

The flowchart illustrates steps of the method following preparatory steps such as, the step of communicatively connecting the control unit to the laboratory instrument(s) of the first group.

Thereafter, in a step 100, the control unit can receive the internal data stream(s) from the laboratory instrument(s) of the first group, the internal data stream(s) comprising data indicative of an operational status of one or more laboratory instrument(s). In subsequent steps 102 and 104, the control unit can process the internal data stream(s) from the laboratory instrument(s) of the first group in order to extract (in step 104) an operational status of one or more laboratory instrument(s) of the first group.

In a—possibly parallel—sequence of steps 200 to 204, the operational status of the laboratory instrument(s) of the second group can be determined. Firstly, in step 200, one or more external surveillance stream(s) of one or more of a second group of laboratory instrument(s) can be captured by one or more surveillance devices. Thereafter, in step 202, the control unit can receive and process the external surveillance stream(s) of the laboratory instrument(s) of the second group to detect (in step 204) an operational status of one or more laboratory instrument(s) of the second group.

In step 300, the operational status of any one of the laboratory instrument(s) of the first and/or second group can be outputted via the lab monitoring interface.

According to further embodiments, the method can compromise capturing a video signal, e.g., a video image, of one or more of the second group of laboratory instrument(s). Accordingly, the step of processing the external surveillance stream(s) of the laboratory instrument(s) of the second group to detect an operational status of one or more laboratory instrument(s) of the second group can comprise one or more of the following: detecting changes of a user interface of the laboratory instrument(s), e.g., changes of color and/or the appearance of one or more icons of bright color; and/or detecting movement and/or position of a part of the laboratory instrument(s), e.g., an open or closed position of compartments for loading consumables of the laboratory instrument(s); and/or detecting visual status indicators, e.g., an emission of status LEDs arranged on a housing of the laboratory instrument(s); and/or capturing a thermal image of one or more of the second group of laboratory instrument(s) and determining an operational temperature of at least a part of the laboratory instrument(s) to determine the operational status of a laboratory instrument, e.g., distinguishing between a normal and abnormal operational status of the respective laboratory instrument(s).

Figure 3:
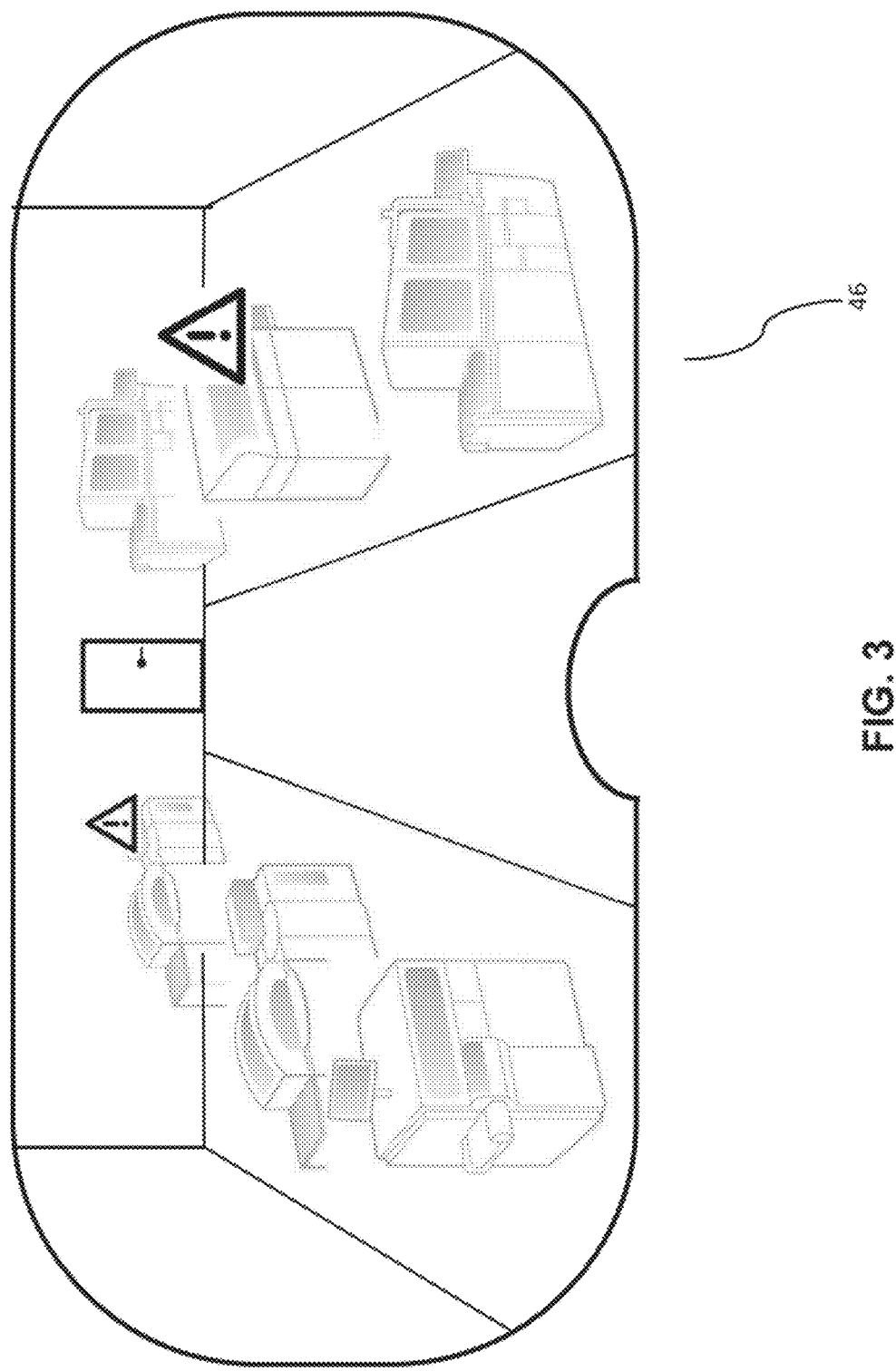
FIG. 3 illustrates an augmented reality device as part of the lab monitoring interface according to an embodiment of the present disclosure.

FIG. 3 shows an embodiment of the disclosed lab monitoring interface 40 comprising an augmented reality device 44. The augmented reality device 44 can be characterized in that it can be designed for producing an overlay 46 of virtual data on (or over) the field of view of an operator. Shown on FIG. 3 is an augmented reality device 44 designed as an optical head-mounted display ("OHMD"), e.g., wearable glasses or goggles.

As depicted in FIG. 3, the overlay can be generated such as to display operational status of a laboratory instrument in the field of view of the operator, the positioning of the operational status allowing the operator to associate the operational status with the respective laboratory instrument. As illustratively shown on FIG. 3, the operational status can be indicated by icons that can be presented as 'floating' above the respective instrument. In some embodiments, icons can be only shown for laboratory instruments that are in an abnormal operation status and the productivity tool can indicate a normal status by not showing an icon in association with instruments having a normal status.

According to some embodiments, the augmented reality device 44 can further comprise a sensor(s) to detect operator interactions to control contents of the overlay. The sensor(s) can comprise cameras, and/or microphones. According to some embodiments, the augmented reality device 44 can be designed for recognizing gaze commands, gesture commands, and/or voice commands. The augmented reality device 44 can comprise an artificial intelligence unit that can be configured to recognize gaze commands, gesture commands, and/or voice commands based on data measured by the sensor(s).

Figure 4:
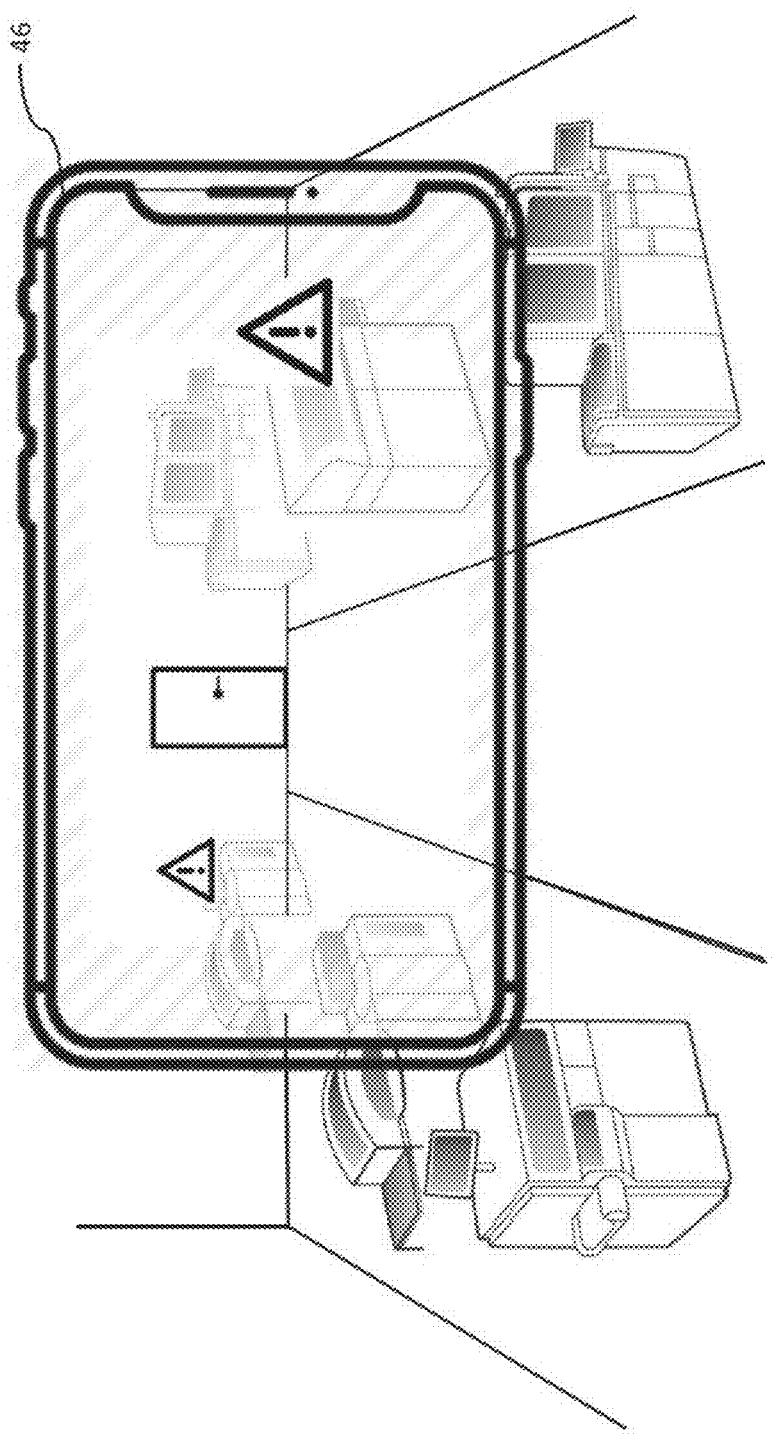
FIG. 4 illustrates an augmented reality device as part of the lab monitoring interface according to another embodiment of the present disclosure.

FIG. 4 shows a further embodiment of the augmented reality device 44 configured as a handheld device (such as a smartphone or a tablet) comprising a camera and a screen, the screen displaying the overlay 46 superimposed over the image of the camera.

Figure 5:
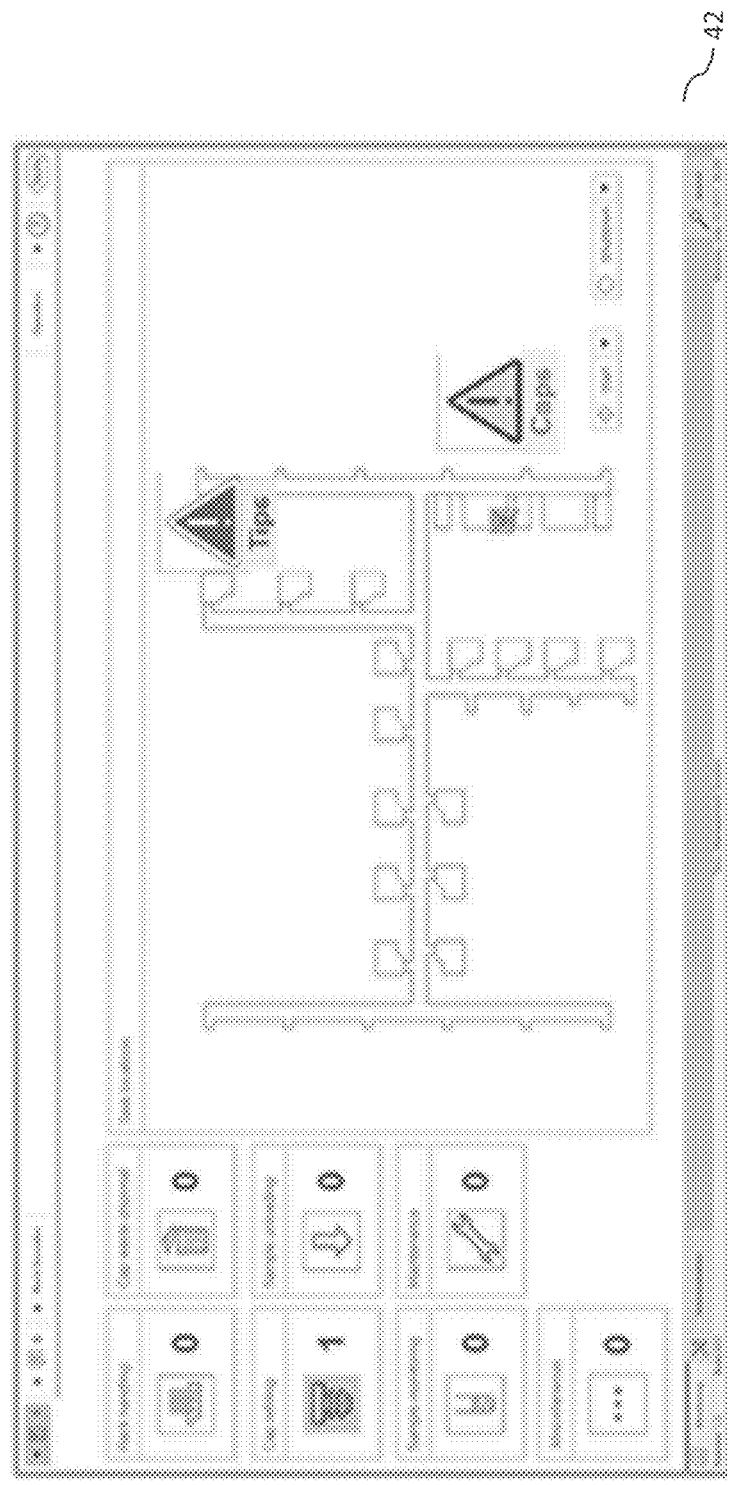
FIG. 5 illustrates an operational status dashboard as part of the lab monitoring interface according to an embodiment of the present disclosure.

FIG. 5 shows a further embodiment of the disclosed lab monitoring interface 40 comprising an operational status dashboard 42 as part of the lab monitoring interface 40, which e.g., can comprise a display on which the dashboard 42 can be displayed. The operational status dashboard 42 can show an aggregation of the operational status of the first group and second group of laboratory instrument(s) 10. The operational status dashboard 42 can be configured to show the operational status of any combination of the laboratory instrument(s) 10 of both the first and second group.

According to some embodiments, the operational dashboard can comprise graphical and/or textual representation of the laboratory instruments. The graphical representation of the laboratory instruments may be shown as a list of icons or thumbnails—optionally grouped by operational status, as shown on the left hand side of FIG. 5. Alternatively, or additionally, the graphical representation of the laboratory instruments may be presented as a map, representative of the physical layout of the laboratory instruments in the laboratory—as shown on the right hand side of FIG. 5.

In an example, the operational status of at least one of the laboratory instrument(s) of the first group can be outputted in form of graphical and/or textual representation via a lab monitoring interface 40 comprising a display at a first time interval and the operational status of at least one of the laboratory instrument(s) of the second group is outputted in the form of graphical and/or textual representation via the display at a second time interval. The first time interval and the second time interval can be overlapping (e.g., identical) or non-overlapping. In an example where the lab monitoring interface 40 comprises an OHMD, the productivity tool can be configured to display the operational status of all the laboratory instrument(s) of the first and of the second group that are currently in the in the field of view of a wearer of the OHMD.

According to further embodiments, the productivity tool 5, e.g., a wearable device (e.g., an OHMD) comprised in the productivity tool 5, can be designed to detect a proximity of an operator to a surveillance device 30. The productivity tool 5, e.g., a wearable device thereof, can e.g., be configured to temporarily disable a surveillance device 30 arranged to capture an external surveillance stream of that particular laboratory instrument(s) 10. This can support protecting the privacy of the operator. According to some embodiments, the productivity tool 5 can be configured to re-enable the surveillance device 30 after the productivity tool 5, e.g., a wearable device thereof, no longer indicates proximity of an operator and/or after expiry of a specified timeout period.

In addition, or alternatively, the productivity tool can be designed to detect, e.g., using a wearable device such as an OHMD, the proximity of an operator to a laboratory instrument(s) 10 being monitored by a surveillance device 30. The productivity tool can be configured to temporarily disable the respective surveillance device 30 if the productivity tool detects that an operator is in proximity (e.g., within 2 meters) of the laboratory instrument(s) 10. In an example, the surveillance device 30 can comprise a video camera and if the productivity tool 5 detects that an operator is in proximity to a laboratory instrument 10 and that the video camera monitoring could have the operator could come into the field of vision of the video camera, the productivity tool 5 can temporarily disable the video camera. According to some embodiments, the productivity tool can be configured to re-enable the surveillance device 30 after the productivity tool no longer detects the operator in the proximity of the laboratory instrument 10.

Figure 6:
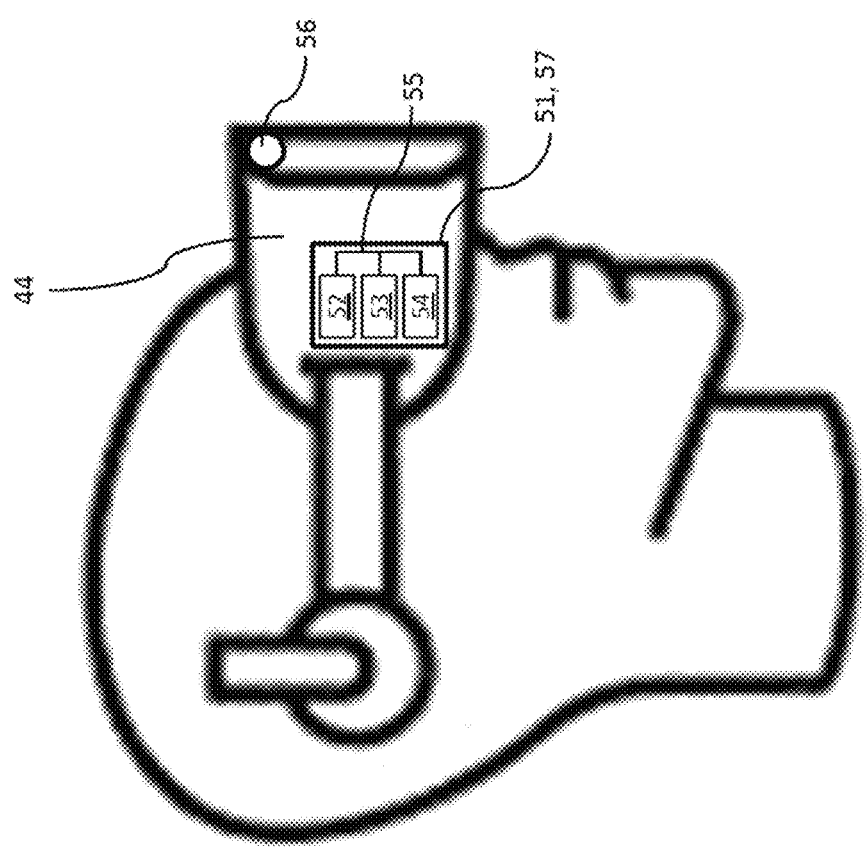
FIG. 6 illustrates an optical head-mounted display (OHMD) according to an embodiment of the present disclosure.

FIG. 6 shows an example of an augmented reality device 44 in the form of an OHMD (an optical head-mounted display). The OHMD can be designed to be worn by a user and for displaying digital images in the field of view of the wearer, thereby creating an augmented reality. An OHMD can e.g., curved mirror based and/or waveguide based. A commercially available OHMD is for example Microsoft's HoloLens. The OHMD can comprise a computer 51 (which can comprise a processor 52, a volatile memory 53, a non-volatile memory 54, and a bus structure 55 connecting these components) for calculating images and the position at which the images are displayed. The OHMD can comprise one or more sensors 56, e.g., for determining the OHMD's position/orientation and/or for determining the position of the wearer's eyes. Data collected by sensors 56 can be used for determining how to display the images so as to create the intended augmented reality. Data collected by sensors 56 can also be used for input, e.g., an eye position sensor can be used for determining gaze commands; a camera can be used for determining gesture commands; and a microphone can be used for determining voice commands. The OHMD, e.g., a computer 51 thereof, can comprise an artificial intelligence unit 57, which can e.g., support calculating the image, calculating the position of the image, and/or recognizing commands.

Further disclosed and proposed is a computer program product including computer-executable instructions for performing the disclosed method in one or more of the embodiments enclosed herein when the program is executed on a computer or computer network. Specifically, the computer program may be stored on a computer-readable data carrier or a server computer. Thus, specifically, one, more than one or even all of the method steps as indicated above may be performed by using a computer or a computer network, e.g., by using a computer program. As used herein, a computer program product refers to the program as a tradable product. The product may generally exist in any format, such as in a downloadable file, on a computer-readable data carrier on premise or located at a remote location (cloud). Specifically, the computer program product may be distributed over a data network (such as a cloud environment). Furthermore, not only the computer program product, but also the execution hardware may be located on-premise or in a cloud environment.

Further disclosed and proposed is a computer-readable medium comprising instructions which, when executed by a computer system, can cause an analytical laboratory to perform the method according to one or more of the embodiments disclosed herein.

Further disclosed and proposed is a modulated data signal comprising instructions, which, when executed by a computer system, cause an analytical laboratory to perform the method according to one or more of the embodiments disclosed herein.

A productivity tool 5 for an analytical laboratory 1 having a plurality of laboratory instrument(s) 10 is proposed. The productivity tool can comprise a control unit 20 communicatively connectable to one or more laboratory instrument(s) 10 of a first group, one or more surveillance device(s) 30 external to the laboratory instrument(s) 10 arranged to capture one or more external surveillance stream(s) of one or more of a second group of laboratory instrument(s) 10, and a lab monitoring interface. The control unit 20 can be configured to receive one or more internal data stream(s) from the laboratory instrument(s) 10 of the first group and one or more external surveillance stream(s) of the laboratory instrument(s) 10 of the second group, the internal data stream(s) comprising data indicative of an operational status of one or more laboratory instrument(s) 10 of the first group; to process the internal data stream(s) from the laboratory instrument(s) 10 of the first group to extract the operational status of one or more laboratory instrument(s) 10 of the first group, to process the external surveillance stream(s) of the laboratory instrument(s) 10 of the second group to detect an operational status of one or more laboratory instrument(s) 10 of the second group, and to output the operational status of any one of the laboratory instrument(s) 10 of the first or second group via the lab monitoring interface.

The surveillance device 30 can comprise a video camera 32 and the external surveillance stream(s) can comprise a video signal of one or more of the second group of laboratory instrument(s) 10. The control unit 20 can be configured to detect an operational status by analyzing the video signal of the one or more of a second group of laboratory instrument(s) 10 to detect changes of a user interface of the laboratory instrument(s) 10 such as, for example, the change of colors, appearance of one or more icon and/or to detect movement and/or position of a part of the laboratory instrument(s) 10 such as, for example, an open or closed position of compartments for loading consumables of the laboratory instrument(s) 10 and/or to detect visual status indicators such as, for example, status LEDs, arranged on a housing of the laboratory instrument(s) 10.

The video camera 32 can be configured to capture a thermal image of one or more of the second group of laboratory instrument(s) 10. The control unit 20 can be configured to determine an operational temperature of a part of the laboratory instrument(s) 10 to determine the operational status of a laboratory instrument 10 such as, for example, to distinguish between a normal and abnormal operational status of the respective laboratory instrument(s) 10.

The surveillance device 30 can comprise a microphone 34 arranged to capture operational noise of one or more of the second group of laboratory instrument(s) 10. The control unit 20 can be configured to determine the operational status of a laboratory instrument 10 by analyzing its operational noise such as, for example, to distinguish between a normal and abnormal operational status of the respective laboratory instrument(s) 10.

The control unit 20 can be configured to aggregate the operational status of the first group and second group of laboratory instrument(s) 10 into an operational status dashboard 42, the operational status dashboard 42 being configured to show the operational status of any combination of the laboratory instrument(s) 10 of both the first and second group.

The productivity tool 5 can further comprise a wearable device configured to detect the proximity of an operator to a surveillance device 30 and configured to temporarily disable the respective surveillance device 30 to protect privacy of the operator.

The lab monitoring interface can comprise an augmented reality device 44 configured to generate an overlay on the field of view of an operator. The overlay can be generated such as to display operational status of a laboratory instrument in the field of view of the operator. The positioning of the operational status allowing the operator to associate the operational status with the respective laboratory instrument.

An analytical laboratory 1 is proposed. The analytical laboratory 1 can comprise one or more laboratory instrument(s) 10 configured to perform one or more processing step(s) on a biological sample and a productivity tool 5 according to the above embodiments.

A computer implemented method for determining operational status of a plurality of laboratory instrument(s) 10 is proposed. The method can comprise communicatively connecting a control unit 20 to one or more laboratory instrument(s) 10 of a first group, capturing one or more external surveillance stream(s) of one or more of a second group of laboratory instrument(s) 10 by a surveillance device 30 and receiving an internal data stream from one or more laboratory instrument(s) 10 of the first group by the control unit. The internal data stream(s) can comprise data indicative of an operational status of one or more laboratory instrument(s) 10 of the first group. The method can also comprise receiving the external surveillance stream(s) of the laboratory instrument(s) 10 of the second group by the control unit, processing the internal data stream(s) from the laboratory instrument(s) 10 of the first group by the control unit to extract an operational status of one or more laboratory instrument(s) 10 of the first group, processing the external surveillance stream(s) of the laboratory instrument(s) 10 of the second group by the control unit to detect an operational status of one or more laboratory instrument(s) 10 of the second group, and outputting the operational status of any one of the laboratory instrument(s) 10 of the first or second group via a lab monitoring interface.

The capturing of the one or more external surveillance stream(s) of one or more of a second group of laboratory instrument(s) 10 by a surveillance device 30 can comprises capturing a video image of one or more of the second group of laboratory instrument(s) 10. The processing of the external surveillance stream(s) of the laboratory instrument(s) 10 of the second group to detect an operational status of one or more laboratory instrument(s) 10 of the second group can comprise one or more of the following: detecting changes of a user interface of the laboratory instrument(s) 10 such as, for example, changes in color, the appearance of one or more icons of bright color and/or detecting movement and/or position of a part of the laboratory instrument(s) 10 such as, for example, an open or closed position of compartments for loading consumables of the laboratory instrument(s) 10 and/or detecting visual status indicators such as, for example, status LEDs, arranged on a housing of the laboratory instrument(s) 10 and/or capturing a thermal image of one or more of the second group of laboratory instrument(s) 10 and determining an operational temperature of a part of the laboratory instrument(s) 10 to determine the operational status of a laboratory instrument 10 such as, for example, distinguishing between a normal and abnormal operational status of the respective laboratory instrument(s) 10.

The method can further comprise capturing operational noise of one or more of the second group of laboratory instrument(s) 10 by a microphone 34 and determining the operational status of a laboratory instrument 10 by analyzing its operational noise such as for example, distinguishing between a normal and abnormal operational status of the respective laboratory instrument(s) 10.

The method can further comprise aggregating the operational status of the first group and second group of laboratory instrument(s) 10 into an operational status dashboard 42. The operational status dashboard 42 can be configured to show the operational status of any combination of the laboratory instrument(s) 10 of both the first and second group.

The method can further comprise generating an overlay 46 on the field of view of an operator using an augmented reality device 44. The overlay can be generated such as to display operational status of a laboratory instrument in the field of view of the operator. The positioning of the operational status can allow the operator to associate the operational status with the respective laboratory instrument.

The method can further comprise detecting proximity of an operator to a laboratory instrument 10 and temporarily disabling the surveillance device 30 arranged to capture an external surveillance stream of that particular laboratory instrument(s) 10 to protect privacy of the operator.

A computer program product is proposed. The computer program product can comprise instructions which, when executed by a control unit 20 of an analytical laboratory 1, can cause the analytical laboratory 1 to perform the above method.

Furthermore, a productivity tool 5 for an analytical laboratory 1 having a plurality of laboratory instrument(s) 10 is proposed. The productivity tool can comprise one or more surveillance device(s) 30 external to the laboratory instrument(s) 10 arranged to capture one or more external surveillance stream(s) of one or more of the plurality of laboratory instrument(s) 10, a lab monitoring interface 40, and a control unit 20 communicatively connectable to the one or more surveillance device(s) 30 and to the lab monitoring interface 40. The control unit 20 can be configured to receive one or more external surveillance stream(s) of one or more of the plurality of laboratory instrument(s) 10, to process the external surveillance stream(s) of the one or more of the plurality of laboratory instrument(s) 10 to detect an operational status of at least one laboratory instrument(s) 10 of the one or more of the plurality of laboratory instrument(s) 10, and to output the detected operational status via the lab monitoring interface 40.

The one or more surveillance device(s) can comprise a camera that can be arranged to monitor a display on which data indicative of an operational status of a laboratory instrument is displayed. This productivity tool can be combined—if compatible and with the according adjustments—with any feature of the other productivity tools proposed herein, in particular with any feature that is connected to the second group (of laboratory instruments) of the other productivity tools proposed herein.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A productivity tool for an analytical laboratory having a plurality of laboratory instrument(s), the productivity tool comprising:
   a control unit communicatively connectable to one or more laboratory instrument(s) of a first group;
   one or more surveillance device(s) external to the laboratory instrument(s) arranged to capture one or more external surveillance stream(s) of one or more of a second group of laboratory instrument(s), the external surveillance data stream(s) independent of the one or more laboratory instruments of the second group; and
   a lab monitoring interface, wherein the control unit is configured to:
   receive one or more internal data stream(s) from the laboratory instrument(s) of the first group and one or more external surveillance stream(s) of the laboratory instrument(s) of the second group, the internal data stream(s) comprising data indicative of an operational status of one or more laboratory instrument(s) of the first group,
   process the internal data stream(s) from the laboratory instrument(s) of the first group to extract the operational status of one or more laboratory instrument(s) of the first group,
   process the external surveillance stream(s) of the laboratory instrument(s) of the second group to detect an operational status of one or more laboratory instrument(s) of the second group,
   output the operational status of any one of the laboratory instrument(s) of the first group via the lab monitoring interface,
   output the operational status of any one of the laboratory instrument(s) of the second group via the lab monitoring interface;
   wherein the one or more surveillance device(s) comprises a video camera and the external surveillance stream(s) comprise a video signal from the video camera capturing video of one or more of the second group of laboratory instrument(s); and
   wherein the control unit is configured to detect an operational status by analyzing the video signal of the one or more of a second group of laboratory instrument(s), wherein the detecting of an operational status comprises detecting changes of a user interface of the one or more of the second group of laboratory instrument(s), wherein the detecting changes of the user interface of the laboratory instrument(s) comprises detecting changes of colors and/or the appearance of one or more icons.

2. The productivity tool for an analytical laboratory according to claim 1, wherein the laboratory instrument(s) of the first group provide a type of data connection for internal data stream(s) that is different from that of the laboratory instrument(s) of the second group.

3. The productivity tool for an analytical laboratory according to claim 1 comprising detecting movement and/or position of at least a part of the laboratory instrument(s) by processing the video signal to detect an open position and/or closed position of compartments for loading consumables of the laboratory instrument(s).

4. The productivity tool for an analytical laboratory according to claim 1 comprising detecting of visual status indicators arranged on a housing of the laboratory instrument(s).

5. The productivity tool for an analytical laboratory according to claim 1, wherein the one or more surveillance device(s) comprises a thermal imaging camera configured to capture a thermal image of one or more of the second group of laboratory instrument(s).

6. The productivity tool for an analytical laboratory according to claim 5, wherein the control unit is configured to analyze images from the thermal imaging camera to determine an operational temperature of at least a part of the laboratory instrument(s) to determine the operational status of a laboratory instrument in order to distinguish between a normal and abnormal operational status of the laboratory instrument(s).

7. The productivity tool for an analytical laboratory according to claim 1, wherein the one or more surveillance device(s) comprise a microphone arranged to capture operational noise of one or more of the second group of laboratory instrument(s).

8. The productivity tool for an analytical laboratory according to claim 7, wherein the control unit is configured to determine the operational status of a laboratory instrument by analyzing the captured operational noise in order to distinguish between a normal and abnormal operational status of the respective laboratory instrument(s).

9. The productivity tool for an analytical laboratory according to claim 1, wherein the productivity tool is configured to display an aggregate of the operational status of the first group and the second group of laboratory instrument(s) in an operational status dashboard, the operational status dashboard being configured to show the operational status of any combination of the laboratory instrument(s) of both the first and second group.

10. The productivity tool for an analytical laboratory according to claim 1, further comprising,
   a wearable device designed to detect the proximity of an operator to a surveillance device and/or to a laboratory instrument monitored by a surveillance device, wherein the productivity tool is configured to temporarily disable the respective surveillance device to protect privacy of the operator.

11. The productivity tool for an analytical laboratory according to claim 1, wherein the lab monitoring interface comprises an augmented reality device designed to generate an overlay of virtual data on a field of view of an operator, the overlay being generated such as to display operational status of a laboratory instrument in the field of view of the operator, wherein positioning of the operational status allows the operator to associate the operational status with the respective laboratory instrument.

12. A computer implemented method for determining operational status of a plurality of laboratory instrument(s), the method comprising:
communicatively connecting a control unit to one or more laboratory instrument(s) of a first group;
capturing one or more external surveillance stream(s) of one or more of a second group of laboratory instrument(s) by one or more surveillance device(s);
receiving an internal data stream from one or more laboratory instrument(s) of the first group by the control unit, the internal data stream(s) comprising data indicative of an operational status of one or more laboratory instrument(s) of the first group, wherein the one or more external surveillance stream(s) are independent of the internal data stream(s);
receiving the external surveillance stream(s) of the laboratory instrument(s) of the second group by the control unit;
processing the internal data stream(s) from the laboratory instrument(s) of the first group by the control unit to extract an operational status of one or more laboratory instrument(s) of the first group;
processing the external surveillance stream(s) of the laboratory instrument(s) of the second group by the control unit to detect an operational status of one or more laboratory instrument(s) of the second group;
outputting the operational status of any one of the laboratory instrument(s) of the first group via a lab monitoring interface; and
outputting the operational status of any one of the laboratory instrument(s) of the second group via a lab monitoring interface;
wherein the one or more surveillance device(s) comprises a video camera and the external surveillance stream(s) comprise a video signal from the video camera capturing video of one or more of the second group of laboratory instrument(s); and
detecting an operational status by analyzing the video signal of the one or more of a second group of laboratory instrument(s), wherein the detecting of an operational status comprises detecting changes of a user interface of the one or more of the second group of laboratory instrument(s), wherein the detecting changes of the user interface of the laboratory instrument(s) comprises detecting changes of colors and/or the appearance of one or more icons.

13. The method according to claim 12, wherein the laboratory instrument(s) of the first group provides a type of data connection for internal data stream(s) that is different from that of the laboratory instrument(s) of the second group.

14. The method according to claim 12, further comprising, capturing operational noise of one or more of the second group of laboratory instrument(s) by a microphone; and determining the operational status of the one or more of the second group of laboratory instrument(s) by analyzing the captured operational noise in order to distinguish between a normal and abnormal operational status of the respective laboratory instrument(s).

15. The method according to one claim 12, further comprising,
detecting proximity of an operator to a laboratory instrument; and
temporarily disabling the surveillance device arranged to capture an external surveillance stream of that particular laboratory instrument(s) to protect privacy of the operator.

16. A productivity tool for an analytical laboratory having a plurality of laboratory instrument(s), the productivity tool comprising:
a control unit communicatively connectable to one or more laboratory instrument(s) of a first group;
one or more surveillance device(s) external to the laboratory instrument(s) arranged to capture one or more external surveillance stream(s) of one or more of a second group of laboratory instrument(s), the external surveillance data stream(s) independent of the one or more laboratory instruments of the second group; and
a lab monitoring interface, wherein the control unit is configured to:
receive one or more internal data stream(s) from the laboratory instrument(s) of the first group and one or more external surveillance stream(s) of the laboratory instrument(s) of the second group, the internal data stream(s) comprising data indicative of an operational status of one or more laboratory instrument(s) of the first group, process the internal data stream(s) from the laboratory instrument(s) of the first group to extract the operational status of one or more laboratory instrument(s) of the first group,
process the external surveillance stream(s) of the laboratory instrument(s) of the second group to detect an operational status of one or more laboratory instrument(s) of the second group,
output the operational status of any one of the laboratory instrument(s) of the first group via the lab monitoring interface,
output the operational status of any one of the laboratory instrument(s) of the output the operational status of any one of the laboratory instrument(s) of the second group via the lab monitoring interface;
wherein the one or more surveillance device(s) comprises a thermal imaging camera configured to capture a thermal image of one or more of the second group of laboratory instrument(s) and wherein the control unit is configured to analyze images from the thermal imaging camera to determine an operational temperature of at least a part of the laboratory instrument(s) to determine the operational status of a laboratory instrument in order to distinguish between a normal and abnormal operational status of the laboratory instrument(s).

17. The productivity tool for an analytical laboratory according to claim 16, wherein the one or more surveillance device(s) comprise a microphone arranged to capture operational noise of one or more of the second group of laboratory instrument(s), wherein the control unit is configured to determine the operational status of a laboratory instrument by analyzing the captured operational noise in order to distinguish between a normal and abnormal operational status of the respective laboratory instrument(s) ..

18. The productivity tool for an analytical laboratory according to claim 16, wherein the productivity tool is configured to display an aggregate of the operational status of the first group and the second group of laboratory instrument(s) in an operational status dashboard, the operational status dashboard being configured to show the operational status of any combination of the laboratory instrument(s) of both the first and second group.

19. The productivity tool for an analytical laboratory according to claim 16, further comprising,
   a wearable device designed to detect the proximity of an operator to a surveillance device and/or to a laboratory instrument monitored by a surveillance device, wherein the productivity tool is configured to temporarily disable the respective surveillance device to protect privacy of the operator.

20. The productivity tool for an analytical laboratory according to claim 16, wherein the lab monitoring interface comprises an augmented reality device designed to generate an overlay of virtual data on a field of view of an operator, the overlay being generated such as to display operational status of a laboratory instrument in the field of view of the operator, wherein positioning of the operational status allows the operator to associate the operational status with the respective laboratory instrument.

* * * * *